(12) United States Patent
Shalyt et al.

(10) Patent No.: US 8,118,988 B2
(45) Date of Patent: Feb. 21, 2012

(54) ANALYSIS OF COPPER ION AND COMPLEXING AGENT IN COPPER PLATING BATHS

(75) Inventors: Eugene Shalyt, Washington Township, NJ (US); Victor Ososkov, Springfield, NJ (US); Michael Pavlov, Fairlawn, NJ (US); Peter Bratin, Flushing, NY (US)

(73) Assignee: ECI Technology, Inc., Totowa, NJ (US)

( * ) Notice: Subject to any disclaimer, the term of this patent is extended or adjusted under 35 U.S.C. 154(b) by 1057 days.

(21) Appl. No.: 12/012,197

(22) Filed: Jan. 31, 2008

(65) Prior Publication Data

US 2009/0194430 A1  Aug. 6, 2009

(51) Int. Cl.
*G01N 31/16* (2006.01)
*C25D 21/16* (2006.01)

(52) U.S. Cl. .......... 205/81; 205/101; 205/296; 205/787; 205/788.5; 436/163

(58) Field of Classification Search .............. 205/81, 205/788.5; 436/163
See application file for complete search history.

(56) References Cited

U.S. PATENT DOCUMENTS

| | | | | |
|---|---|---|---|---|
| 4,789,648 A * | 12/1988 | Chow et al. | | 438/633 |
| 5,151,168 A * | 9/1992 | Gilton et al. | | 205/123 |
| 5,209,817 A * | 5/1993 | Ahmad et al. | | 216/18 |
| 6,197,181 B1 * | 3/2001 | Chen | | 205/123 |
| 6,277,263 B1 * | 8/2001 | Chen | | 205/182 |
| 6,287,445 B1 * | 9/2001 | Lashmore et al. | | 205/144 |
| 6,890,758 B2 * | 5/2005 | Shalyt et al. | | 436/163 |
| 6,913,686 B2 * | 7/2005 | Hilgarth | | 205/788.5 |
| 6,919,013 B2 * | 7/2005 | Chen | | 205/182 |
| 7,135,404 B2 * | 11/2006 | Baskaran et al. | | 438/652 |
| 7,323,421 B2 * | 1/2008 | Stinson et al. | | 438/749 |

FOREIGN PATENT DOCUMENTS

| | | | |
|---|---|---|---|
| JP | 60-104248 | * | 6/1985 |
| JP | 63-176477 | * | 7/1988 |

* cited by examiner

*Primary Examiner* — Alexa Neckel
*Assistant Examiner* — William Leader
(74) *Attorney, Agent, or Firm* — D. Morgan Tench

(57) ABSTRACT

A simple titration method involving a single copper ion titrant detected by a copper ion specific electrode provides the concentrations of both copper ions and bath complexing agent (ethylene diamine, for example) in alkaline copper electroplating baths of the type used to deposit or thicken copper seed layers on silicon wafers. Standard addition of an excess of a strong complexing agent (EDTA, for example) and backtitration with the copper ion titrant yields the bath copper ion concentration, and continued titration to a second endpoint, preferably after addition of hydroxide to adjust the pH of the analysis solution, yields the total concentration of bath complexing agent. Based on these analyzes, the concentration of free bath complexing agent may be calculated. The method also provides direct determination of the free bath complexing agent concentration via standard addition of excess bath complexing agent to a sample of the plating bath and titration with the copper ion titrant.

15 Claims, 5 Drawing Sheets

ANALYSIS OF COPPER ION AND COMPLEXING AGENT IN COPPER PLATING BATHS

BACKGROUND OF THE INVENTION

1. Field of the Invention

This invention is concerned with analysis of alkaline copper electroplating baths as a means of providing control over the deposit properties.

2. Description of the Related Art

Copper is the preferred metallization for providing electrical interconnections on high-speed semiconductor chips due to its high electrical conductivity and good electromigration resistance compared to aluminum. However, copper is more difficult to pattern than aluminum so that it has been necessary to develop alternative methods for forming copper circuitry on semiconductor substrates. The leading technology for fabricating copper integrated circuit (IC) chips is the "Damascene" process (P. C. Andricacos, Electrochem. Soc. Interface, Spring 1999, p. 32; U.S. Pat. No. 4,789,648 to Chow et al.; U.S. Pat. No. 5,209,817 to Ahmad et al.), which depends on copper electroplating to provide complete filling of the fine features involved.

In the Damascene process, fine trenches and vias are patterned and etched into a dielectric layer of silicon dioxide on a silicon wafer using standard photoresist techniques. Copper is ultimately electrodeposited within the trenches and vias to form the circuitry but a barrier layer must be used to prevent migration of copper ions into the silicon dioxide dielectric material. The barrier layer is typically 100 to 300 Å of titanium nitride or tantalum nitride deposited by a physical vapor deposition (PVD) or chemical vapor deposition (CVD) method. A seed layer of copper, typically deposited by a PVD or CVD method, is usually needed to promote adhesion between the barrier layer material and the copper electrodeposited within the trenches and vias to form the circuitry. Copper electrodeposition is generally performed from an acid copper sulfate electroplating bath containing organic additives that provide complete filling of the Damascene features (trenches and vias).

Seed layers deposited by PVD or CVD methods tend to be thicker near the outsides of the Damascene features and thinner on the sidewalls and bottoms. Copper seed layers also undergo chemical dissolution in contact with the acidic plating bath on open circuit, before a cathodic voltage is applied to plate copper. The surface oxide formed on the seed layer in contact with air prior to copper plating dissolves rapidly in the acidic bath, resulting in a loss of seed layer copper. Consequently, a seed layer thickness of about 1000 Å is needed to provide adequate coverage of the barrier layer and good adhesion of the electrodeposited copper.

As the dimensions of Damascene features have been extended into the submicron region, the nonuniformity of PVD and CVD seed layers has become a significant problem. In particular, greater seed layer thickness near the top of a feature tends to pinch-off the feature entrance, further reducing the seed layer thickness on the sidewalls and bottom. The subsequent copper electrodeposition process is adversely affected by both the reduced seed layer thickness and restricted electrolyte flow within features so that complete filling of very fine features is not attained.

Prior art approaches to addressing this problem have involved developing an alkaline bath for electroplating uniform copper layers directly on the barrier layer, or on an ultra-thin copper seed layer (used to promote adhesion to the barrier layer). The alkaline bath provides a conformal copper coating of uniform thickness so that a thicker copper seed layer can be deposited without pinching-off the trenches. In addition, copper does not readily dissolve in the alkaline solution and surface copper oxides tend to be reduced back to adherent metal at the beginning of the electrodeposition process so that seed layer loss in the alkaline bath is minimal. The alkaline bath typically operates at a relatively low current density and is only used to provide a conformal copper seed layer of sufficient thickness to survive in an acid copper bath, which is used to rapidly fill the Damascene features.

U.S. Pat. No. 5,151,168 to Gilton et al. describes an alkaline copper electroplating bath for depositing conformal copper coatings directly on barrier layer materials, such as titanium nitride, titanium-tungsten or nitrided titanium-tungsten. In a preferred embodiment, the bath comprises 0.035 M cupric sulfate and 0.07 M sodium ethylenediaminetetraacetate (NaEDTA) complexing agent (pH 13.5), and is operated at 1 mA/cm$^2$ at 25° C.

U.S. Pat. Nos. 6,197,181, 6,277,263 and 6,919,013 to Chen describe an alkaline copper electroplating bath for conformally enhancing an ultra-thin copper seed layer (preferably 200 Å thick and deposited by a PVD method) for subsequent Damascene plating from an acid copper electroplating bath. The disclosed alkaline plating bath comprises cupric sulfate (0.03 to 0.25 M), a complexing agent (molar ratio of 1 to 4 relative to copper ion), and potassium hydroxide, ammonium hydroxide, tetraethylammonium hydroxide or sodium hydroxide (pH at least 9.0). The bath preferably also includes 0.01 to 0.5 M boric acid to aid in maintaining pH and/or to improve deposit quality. Salts with electrochemically unreactive cations, 0.01 to 0.5 M ammonium sulfate, for example, may be added to increase the electrolyte conductivity so as to reduce the sheet resistance. In this case, it may be advantageous to add an agent, such as ethylene glycol, to enhance the conformality of the deposited copper layer.

Suitable complexing agents disclosed by Chen ('181, '263 and '013) consist of ethylene diamine (EDA), ethylene diamine tetraacetic acid (EDTA), a polycarboxylic acid, such as citric acid, and salts thereof. These complexing agents may be used in combination with each other or with other complexing agents. Preferred pH values are 9.5 for baths containing citric acid or EDA as the complexing agent, and 12.5 for baths employing the EDTA complexing agent. The bath may be operated at a temperature in the range 20° to 35° C. (preferably 25° C.), and a current density in the range 1 to 5 mA/cm$^2$ (preferably 1 to 2 mA/cm$^2$) may be used. The copper layer plated on the seed layer from the alkaline copper bath preferably has a thickness in the 400 to 800 Å range.

One preferred plating bath according to Chen ('181, '263 and '013) has a pH of 9.5 and comprises 0.1 M cupric sulfate (CuSO$_4$), 0.2 M citric acid and 0.05 M boric acid (H$_3$BO$_3$). Another preferred plating bath according to Chen ('181, '263 and '013) has a pH of 9.5 and comprises 0.25 M cupric sulfate, 0.5 M EDA, 0.2 M boric acid and 0.3 M ammonium sulfate. Yet another preferred plating bath according to Chen ('181, '263 and '013) has a pH of 12.5 and comprises 0.1 M cupric sulfate, 0.2 M EDTA and 0.05 M boric acid.

U.S. Pat. No. 7,135,404 to Baskaran et al. describes an alkaline copper electroplating bath for Damascene seed layer applications having the same constituents as that of Chen ('181, '263 and '013) but with extended concentration limits. According to Baskaran '404, suitable alkaline copper baths for depositing conformal copper coatings with good adhesion comprise cupric sulfate (0.004 to 1.0 M), complexing agent (molar ratio of 1 to 4 relative to copper ion), boric acid (0.001 to 0.5 M) and tetramethylammonium hydroxide (pH 9.5 to 12.5). A bath comprising 10 g/L cupric sulfate, an ethylene diamine (EDA) complexing agent (molar ratio of 2 relative to copper ion), 3.1 g/L boric acid and tetraethylammonium hydroxide (pH 9.5) is reportedly suitable for depositing seed layers directly on barrier layer materials. Baskaran '404 also discloses that the source of copper ions in the plating bath may be copper sulfate, copper gluconate, sodium copper cyanide, copper sulfamate, copper chloride, copper citrate, copper fluoroborate or copper pyrophosphate. Baskaran '404 further discloses that the alkaline copper electroplating bath may also include an alloying metal selected from the group consisting of chromium, nickel, cobalt, zinc, aluminum, boron, magnesium and cerium. A suitable bath for plating a copper-chromium alloy seed layer directly on barrier layer materials reportedly comprises $CrSO_4$ (10-40 g/L), $CuSO_4$ (5-20 g/L), $(NH_4)_2SO_4$ (20-40 g/L), $NH_4OH$ (50-100 mL/L), and EDA or EDTA (0.1-1.0 mL/L).

Such prior art alkaline plating baths are intended to provide the conformal copper seed layers needed for complete filling of very fine Damascene trenches and vias with void-free copper having good adhesion to the barrier layer. In order to obtain consistently good results, the concentrations of the key constituents in the plating bath, copper ions and the complexing agent, must be closely controlled. It is likely that a titration method based on a specific complexing agent titrant could be developed to measure the copper ion concentration, and that a titration method based on a metal ion titrant could be developed to measure the complexing agent concentration. However, such an approach is undesirable since Damascene plating processes, including the plating bath analyses, must be highly automated, and use of multiple reagents renders automation more difficult. In addition, it is desirable to minimize the waste stream from the Damascene process for environmental reasons. Consequently, a simple method is needed for measuring the copper ion and complexing agent concentrations in alkaline copper electroplating baths.

SUMMARY OF THE INVENTION

The invention provides a method and an apparatus for determining the concentrations of copper ions and a copper complexing agent present in an alkaline copper electroplating bath. The copper complexing agent is termed the bath complexing agent, which functions to stabilize copper ions in the alkaline copper plating bath. The invention is especially suitable for analysis of the type of copper plating baths used to provide conformal copper seed layers of sufficient thickness and adhesion for acid copper plating of semiconductor wafers in the Damascene process. Copper plating baths of this type typically have a pH in the range from 9 to 13, and comprise copper ions having a concentration in the range from 0.001 to 1.0 M (preferably added as cupric sulfate), a copper complexing agent (preferably ethylene diamine or citric acid, or salts thereof) having a molar ratio in the range from 1 to 4 relative to the copper ion concentration, and optionally boric acid having a concentration in the range from 0.001 to 0.5 M.

In a preferred embodiment of the invention, a simple two-stage titration method involving a single copper ion titrant (comprising free $Cu^{2+}$ ions) detected in an analysis solution by a copper ion specific electrode or other means provides the concentrations of both copper ions and bath complexing agent (ethylene diamine, for example) in an alkaline copper electroplating bath. Standard addition of a stoichiometric excess of a strong copper complexing agent (EDTA, for example) and back-titration with the copper ion titrant yields the bath copper ion concentration, and continued titration to a second endpoint, optionally after addition of hydroxide to adjust the pH of the analysis solution, yields the total concentration of bath complexing agent. In this case, the concentration of free bath complexing agent may be calculated from the total concentrations of copper ions and bath complexing agent determined by the two-stage titration.

In a basic embodiment, the invention further provides a method and an apparatus for directly determining the concentration of free bath complexing agent in a copper plating bath. In this case, a stoichiometric excess of the bath complexing agent is added by standard addition to a separate sample of the copper plating bath and the excess bath complexing agent in the resulting analysis solution is titrated with a copper ion titrant (comprising free $Cu^{2+}$ ions). This basic embodiment of the invention may be used in combination with the method of the invention for determining the concentration of copper ions in the copper plating bath, or with any other method for determining the copper ion concentration, direct titration with EDTA, for example.

The apparatus of the invention enables automated application of the method of the invention. The apparatus comprises a computing device that is interfaced with suitable electronic and mechanical equipment, and includes a memory element with a stored algorithm operative to effect at least the basic steps of at least one embodiment of the method of the invention.

The invention is useful for improving the quality and yield of high-speed integrated circuit chips employing copper circuitry by providing a method and an apparatus for controlling the copper ion and complexing agent concentrations in alkaline plating baths used to provide conformal copper seed layers. A key feature of the invention is that the concentrations of copper ion and bath complexing agent in the copper plating bath may be measured using a single titrant solution (or separate titrant solutions containing the same titrant species at different concentrations). Use of a single titrant for both analyses minimizes the waste stream and greatly simplifies automation of the bath analysis system. Furthermore, the invention may be practiced using only one additional reagent (a complexing agent), further reducing the waste stream and simplifying the analysis. The method of the invention may be performed rapidly and generates a minimal waste stream compared to potential alternative methods.

Further features and advantages of the invention will be apparent to those skilled in the art from the following detailed description, taken together with the accompanying drawings.

DETAILED DESCRIPTION OF THE INVENTION

Figure 1:
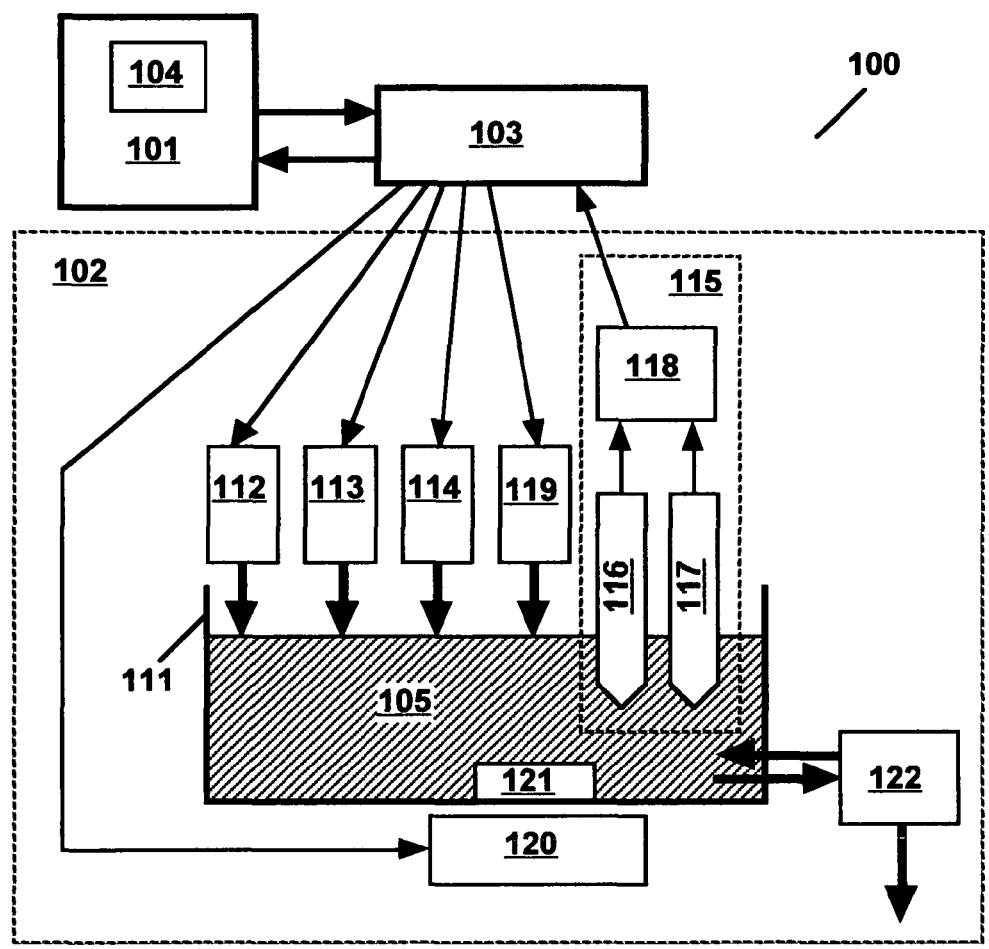
FIG. 1 is a schematic representation of a preferred apparatus of the invention.

Technical terms used in this document are generally known to those skilled in the art. The terms "electroplating", "plating" and "electrodeposition" refer to copper electrodeposition and are equivalent. The terms "alkaline copper electroplating bath", "copper plating bath" and "plating bath" are used interchangeably. The term "complexing agent" always refers to complexation of copper ions. The term "bath complexing agent" refers to the complexing agent present in an alkaline copper plating bath to stabilize copper ions in the copper plating bath so as to prevent precipitation of copper compounds, copper hydroxide, for example, and to increase the copper electrodeposition potential so as to improve the deposit properties. The term "EDTA" encompasses ethylenediaminetetraacetic acid, as well as any of its salts, including $Na_4EDTA$, $Na_3HEDTA$, $Na_2H_2EDTA$ and $NaH_3EDTA$, for example, and analogous salts involving other cations, potassium ions, for example.

As recognized by those skilled in the art, there are different degrees of copper ion complexation, depending on the complexing agent and the solution environment. For a titration or back-titration involving a free $Cu^{2+}$ ion titrant, the endpoint is typically detected as a substantial increase in a measured $Cu^{2+}$ ion concentration parameter, the potential of a copper ion specific electrode, for example. This parameter is proportional to the "free" copper ion concentration and theoretically could be converted to an actual $Cu^{2+}$ concentration. Such a conversion, however, is tenuous when the $Cu^{2+}$ concentration is determined by equilibria involving one or more complexing agents, and is unnecessary with respect to determining titration and back-titration endpoints. In this document, the terms "free copper ions" or "free" with respect to copper ions denotes copper ions that are sufficiently uncomplexed to be detected by the detection means employed. The "free copper ions" in this case may be complexed by fewer complexing agent molecules per copper ion, or by a relatively weak complexing agent, a bath complexing agent rather than a strong complexing agent, for example. Likewise, an amount of "free complexing agent" in a solution corresponds to the molar-equivalent amount of free copper ions that would need to be added before free copper ions would produce a substantial increase in $Cu^{2+}$ concentration parameter measured by the detection means employed. The term "$Cu^{2+}$ concentration parameter" encompasses an actual concentration.

The term "standard addition" generally means addition of a predetermined quantity of a species (a complexing agent, for example) to a predetermined volume of a solution (a sample of a plating bath, for example). The predetermined quantity may be a predetermined weight of the species or a predetermined volume of a standard solution containing the species. A "standard solution" comprises a precisely known concentration of a reagent used for a chemical analysis. The symbol "M" means molar concentration.

A "titrant solution" is a standard solution comprising a known concentration of a reagent called a "titrant" that chemically reacts with a "reactant" or "unknown species" whose concentration in a sample solution is to be determined. A "titration" is an analytical procedure involving repeated standard addition of a known volume of a titrant solution to an analysis solution (comprising the sample solution), coupled with monitoring the concentration of an indicator species, which participates in the reaction between the titrant and the reactant, or is indirectly affected by this reaction.

The "equivalence point" is the point in a titration at which the reaction between the titrant and the reactant is complete, corresponding to a stoichiometric balance between the number of moles of the titrant and the number of moles of the reactant with respect to formation of a compound or complex. The "titration endpoint" corresponds to a relatively rapid change in the concentration of the indicator species as additional titrant is added to the analysis solution after the equivalence point has been reached. The concentration of the unknown species in the sample solution is calculated from the volume of titrant solution added to the analysis solution at the equivalence point (approximately equivalent to the endpoint). A "back-titration" involves standard addition (to an analysis solution) of a back-titration reagent that reacts with the unknown species. An excess of the back-titration reagent is added to the analysis solution and then reacted with a titrant in a titration back to the equivalence point.

A "titration curve" is a plot of the concentration of a titration indicator species in an analysis solution, or a parameter proportional to this concentration, as a function of the volume of titrant solution added to the analysis solution. It is typically more convenient to utilize a concentration parameter that is proportional to the concentration of the indicator species, especially when the indicator species participates in a complexation reaction involving competing complexing agents. The endpoint for the titration is typically determined from a curve feature corresponding to a rapid change in the concentration of the indicator species, such as a curve knee or inflection point. Detection of the titration endpoint may be facilitated by differentiating the titration curve, which converts an inflection point into a peak. Titration data are typically handled as titration curves or plots but such data may be tabulated and used directly, especially by a computer, and the term "titration curve" includes tabulated data.

The invention provides a method and an apparatus for analysis of alkaline copper electroplating baths that have a pH in the range from 8 to 14, and comprise copper ions having a concentration in the range from 0.001 to 1.0 M, a bath complexing agent having a molar ratio in the range from 1 to 4 relative to the copper ion concentration, and optionally boric acid having a concentration in the range from 0.001 to 0.5 M. The invention may be used to determine the concentrations of copper ions, total bath complexing agent and free bath complexing agent in alkaline copper plating baths.

The basic method and apparatus of the invention may be used to determine the free complexing agent concentration for any copper plating bath employing any suitable bath complexing agent. The free complexing agent determination of the invention may be used in conjunction with any suitable method for determining the copper ion concentration, including direct titration with a strong complexing agent, EDTA, for example.

Preferred embodiments of the invention, however, allow the copper ion concentration and the free and total bath complexing agent concentrations to be determined using the same copper ion titrant. Such preferred embodiments may be applied to analyze copper plating baths employing any bath complexing agent for which a substantially stronger complexing agent can be identified. Preferred bath complexing agents include ethylene diamine (EDA), citric acid, and salts thereof. The invention may be applied to analysis of alkaline copper baths employing a wide variety of complexing agents, a polycarboxylic acid, such as tartaric acid, nitrilotriacetic acid (NTA) or ethylenediaminetetraacetic acid (EDTA), or an amine, such as triethanolamine (TEA), or an imide, such as succinimide, or salts thereof, for example.

Copper ions in the copper plating bath analyzed by the method of the invention may be derived from any suitable salt, including copper sulfate, copper gluconate, sodium copper cyanide, copper sulfamate, copper chloride, copper citrate, copper fluoroborate or copper pyrophosphate. Any suitable hydroxide may be used to adjust the pH of the copper plating bath including sodium hydroxide, potassium hydroxide, ammonium hydroxide, and a tetraalkylammonium hydroxide, for example. The copper plating bath may also include unreactive salts to increase the electrolyte conductivity, ammonium sulfate, for example, or an agent to enhance the conformality of the deposited copper layer, such as ethylene glycol, or both. The invention may also be used to analyze alkaline copper alloy electroplating baths, containing ions of chromium, nickel, cobalt, zinc, aluminum, boron, magnesium or cerium, for example.

The invention is especially suitable for analysis of alkaline copper plating baths formulated to provide conformal copper seed layers of sufficient thickness and adhesion for acid copper plating of semiconductor wafers in the Damascene process. However, the invention may be used for analysis of alkaline copper plating baths formulated for any suitable application. The analysis of the invention may be used to determine the concentrations of copper ions, free bath complexing agent and/or total bath complexing agent in copper plating baths.

In a preferred method of the invention, a simple two-stage titration procedure involving a single copper ion titrant and measurement of a $Cu^{2+}$ concentration parameter in an analysis solution comprising a sample of a copper plating bath provides the concentrations of both copper ions and a bath complexing agent in the copper plating bath. Standard addition of a stoichiometric excess of a strong complexing agent to the analysis solution and back-titration with the copper ion titrant to a back-titration endpoint (back-titration stage) yields the bath copper ion concentration, and continued titration to a second endpoint (titration stage) yields the total concentration of the bath complexing agent. The strong complexing agent is selected to be sufficiently strong to displace the bath complexing agent so as to complex substantially all of the copper ions in the analysis solution. Preferably, addition of the strong complexing does not substantially change the pH of the analysis solution and/or the pH is adjusted by addition of an appropriate compound, initially or after the first stage of the titration.

During the back-titration stage of the method of the invention, the measured $Cu^{2+}$ concentration parameter is very small and increases only slowly as free $Cu^{2+}$ ions from the added titrant solution react with the excess strong complexing agent added by standard addition. After the excess strong complexing agent is consumed, at the equivalence point of the back-titration, the $Cu^{2+}$ concentration parameter increases relatively rapidly to a value corresponding to weaker copper complexation by the bath complexing agent, indicating the endpoint of the back-titration.

During the titration stage of the method of the invention, continued addition of the copper ion titrant after the back-titration endpoint produces a relatively slow increase in the measured $Cu^{2+}$ concentration parameter due to reaction of the free $Cu^{2+}$ ions from the added titrant with free bath complexing agent, liberated by addition of the strong complexing agent prior to the back-titration. After the excess bath complexing agent is consumed, at the equivalence point of the titration, the $Cu^{2+}$ concentration parameter again increases relatively rapidly due to an increasing concentration of free $Cu^{2+}$ ions as additional titrant solution is added to the analysis solution, indicating the endpoint of the titration.

The concentration of free bath complexing agent may be calculated from the total concentrations of copper ions and bath complexing agent determined by the back-titration and titration of the method of the invention. The method also provides direct determination of the free bath complexing agent concentration via standard addition of excess bath complexing agent to a separate sample of the plating bath, and titration with a copper ion titrant.

A preferred method for analyzing a copper plating bath comprising copper ions and a bath complexing agent according to the invention, comprises the steps of: (1) making a standard addition of a predetermined quantity of a strong complexing agent to a first sample of the copper plating bath so as to provide a first analysis solution of known volume contained in a first analysis cell, said predetermined quantity of the strong complexing agent being substantially greater than that needed to fully complex all of the copper ions present in the first analysis solution; (2) providing a first titrant solution comprising a first predetermined concentration of copper ions; (3) performing a back-titration by repeatedly adding an aliquot of a known volume of the first titrant solution to the first analysis solution and measuring a first $Cu^{2+}$ concentration parameter for the first analysis solution; (4) determining a back-titration endpoint corresponding to a substantial increase in the first $Cu^{2+}$ concentration parameter measured for the first analysis solution; (5) calculating the concentration of copper ions in the copper plating bath based on the back-titration endpoint; (6) providing a second analysis solution contained in a second analysis cell; (7) providing a second titrant solution comprising a second predetermined concentration of copper ions; (8) performing a titration by repeatedly adding an aliquot of a known volume of the second titrant solution to the second analysis solution and measuring a second $Cu^{2+}$ concentration parameter for the second analysis solution; (9) determining a titration endpoint corresponding to a substantial increase in the second $Cu^{2+}$ concentration parameter measured for the second analysis solution; and (10) calculating a concentration of the bath complexing agent based on the titration endpoint. The Steps (1)-(10) of the preferred method of the invention may be performed using standard analytical techniques and equipment and are meant to be self-explanatory to those skilled in the art.

The order in which the steps of the invention are performed may be varied. Steps (1)-(10) of the preferred method of the invention may be performed in the order given, or in any suitable order. Steps (1) and (2) may be performed in either order, but must be performed before Step (3). Steps (6) and (7) may be performed in either order, but must be performed before Step (8). Steps (4) and (5) must be performed in order but may be performed after Step (8) or after Step (10), for example.

Steps (1)-(5) comprise the back-titration stage of the preferred method of the invention, which provide the total copper ion concentration in the copper plating bath. At the beginning of the back-titration, the first analysis solution comprises a bath sample and a stoichiometric excess of the strong complexing agent (added by standard addition). During the back-titration, free $Cu^{2+}$ ions added to the first analysis solution from the titrant solution react with the excess strong complexing agent so that the measured $Cu^{2+}$ concentration parameter remains very low until the excess strong complexing agent is consumed (at the equivalence point). As addition titrant is added, the $Cu^{2+}$ concentration parameter and then rises relatively rapidly, indicating the endpoint of the back-titration At the equivalence point for the back-titration, substantially all of the copper ions in the second analysis solution are complexed by the strong complexing agent. In this case, the total number of moles of copper ions (free and complexed) initially present in the second bath sample (which can be used to calculate the copper ion concentration in the plating bath) is given by the equation:

$$\text{moles copper ions in bath sample} = (1/MR_1)(\text{moles SCA added}) - \text{moles } Cu^{2+} \text{ titrated}$$

where SCA is the strong complexing agent and $MR_1$ is the molar ratio of the strong complexing agent per complexed copper ion. The molar concentration of copper ions in the copper plating bath is the number of moles of copper ions in the bath sample divided by the volume of the bath sample.

The strong complexing agent may be any complexing agent that is substantially stronger than the bath complexing agent and is chemically compatible with the copper plating bath. Ethylenediaminetetraacetic acid and its salts, all of which are encompassed by the acronym EDTA, are sufficiently strong copper complexing agents to be generally useful for the method of the invention. Addition of acidic EDTA species, however, tends to lower the pH of the alkaline analysis solution due to liberation of protons as the acidic EDTA species reacts with $Cu^{2+}$ ions. The lower pH may inhibit copper complexation by the bath complexing agent (EDA, for example) and interfere with the bath complexing agent titration. Consequently, less acidic EDTA species, $Na_4EDTA$ or $Na_2H_2EDTA$, for example, are preferred for use as strong complexing agents according to the invention. Note that addition of NaOH (or another hydroxide compound) and $Na_2H_2EDTA$ in the molar ratio 2:1 is equivalent to adding $Na_4EDTA$.

Steps (6)-(10) comprise the titration stage of the preferred method of the invention, which may provide either the free or total concentration of the bath complexing agent, depending on the composition of the second analysis solution of Step (6). The second analysis solution used for the titration stage may comprise the analysis solution used for the back-titration, or a separate (second) sample of the plating bath.

The total concentration of the bath complexing agent is provided when the second analysis solution comprises the first analysis solution from Step (3). In this case, the same bath sample and the same analysis cell are used for both the back-titration of Step (3) and the titration of Step (8). At the beginning of the titration, all of the copper ions in the analysis solution are complexed by the strong complexing agent and all of the bath complexing agent (including the fraction initially complexed by copper in the plating bath sample) is present as free bath complexing agent in the analysis solution. The bath complexing agent was displaced from copper complexes by the strong complexing agent added prior to the back-titration.

During the titration, free $Cu^{2+}$ ions from the titrant react with the free bath complexing agent so that the $Cu^{2+}$ concentration parameter remains relatively low until the free bath complexing agent is consumed (at the equivalence point), then rises relatively quickly as additional titrant is added, indicating the endpoint of the titration.

At the equivalence point, the total number of moles of the bath complexing agent (BCA) in the copper bath sample is given by the equation:

$$\text{total moles BCA} = 1/MR_2 (\text{moles of } Cu^{2+} \text{ added during titration stage})$$

where $MR_2$ is the molar ratio of bath complexing agent per copper ion. The molar concentration of the bath complexing agent in the copper plating bath is the number of moles of the bath complexing agent in the bath sample divided by the volume of the bath sample.

In another preferred embodiment of the preferred method of the invention, the second analysis solution of Step (6) comprises the first analysis solution from Step (3) and a predetermined quantity of a hydroxide compound is added by standard addition to the first analysis solution so as to provide a pH for the second analysis solution that enhances copper complexation by the bath complexing agent. For example, a hydroxide compound may be added to the first analysis solution to compensate for a decrease in pH resulting from addition of an acidic EDTA strong complexing agent. The hydroxide compound may be any suitable hydroxide salt, including sodium hydroxide, potassium hydroxide, ammonium hydroxide or a tetraalkylammonium hydroxide, for example. Addition of a hydroxide compound may be used in combination with a less acidic strong complexing agent species to enhance copper complexation by the bath complexing agent. The hydroxide compound may be added to the first analysis solution before or after the back-titration stage comprising Steps (1)-(5).

The titration stage comprising Steps (6)-(10) of the preferred method of the invention provides the free bath complexing agent concentration when the second analysis solution comprises a second sample of the plating bath and a stoichiometric excess of the bath complexing agent relative to the copper ion concentration. A sufficient quantity of the bath complexing agent is added by standard addition to the second bath sample to provide, in combination with the bath complexing agent already present in the second bath sample, the stoichiometric excess of the bath complexing agent in the second analysis solution. At the beginning of the titration, all of the copper ions in the second analysis solution are complexed with the bath complexing agent (in lieu of a stronger complexing agent) and free bath complexing agent is present.

During the titration, $Cu^{2+}$ ions from the titrant react with the free bath complexing agent in the second analysis solution so that the $Cu^{2+}$ concentration parameter remains relatively low until the free bath complexing agent is consumed (at the equivalence point). The $Cu^{2+}$ concentration then rises relatively quickly as additional titrant is added, indicating the endpoint of the titration.

At the equivalence point for the titration, substantially all of the copper ions in the second analysis solution are complexed by the bath complexing agent. In this case, the total number of moles of bath complexing agent (BCA), free and copper complexed, in the plating bath sample is given by the equation:

total moles BCA in sample=$MR_2$(moles $Cu^{2+}$ in sample+moles $Cu^{2+}$ titrated)−moles BCA added which may be rewritten as:

moles free BCA in sample=total moles BCA in sample−$MR_2$(moles $Cu^{2+}$ in sample)=$MR_2$ (moles $Cu^{2+}$ titrated)−moles BCA added, where $MR_2$ is the molar ratio of bath complexing agent per complexed copper ion. The molar concentration of free bath complexing agent in the copper plating bath is the number of moles of free bath complexing agent in the bath sample divided by the volume of the bath sample.

In a basic embodiment of the invention, Steps (6)-(10) may be performed as an independent analysis to determine the concentration of free bath complexing agent in a copper plating bath. In this case, the analysis solution comprises a sample of the plating bath and a stoichiometric excess of the bath complexing agent. The free bath complexing agent concentration determined by the basic embodiment is an important control parameter for alkaline copper plating baths. Within the scope of the invention, however, the total bath complexing agent concentration [total BCA] in the copper plating bath may be calculated using the measured values for the free bath complexing agent concentration [free BCA] and the total copper ion concentration [total $Cu^{2+}$] in the copper plating bath, according to the equation:

[total BCA]=[free BCA]+($MR_2$)[total $Cu^{2+}$]

where $MR_2$ is the molar ratio of bath complexing agent per complexed copper ion. For the basic embodiment, the total copper ion concentration may be determined by any suitable method, direct titration with EDTA, for example.

The first and second titrant solutions for the preferred embodiment of the invention may have different chemical compositions but are preferably the same solution or differ only in the concentration of copper ions, which may be adjusted to provide optimum sensitivity and precision for the copper ion and free bath complexing agent analyses. The source of copper ions in the titrant solutions is preferably cupric sulfate but could be any cupric salt, cupric nitrate or cupric perchlorate, for example, whose anions are sufficiently weak complexing agents to provide relatively free $Cu^{2+}$ ions compared to the bath complexing agent. The copper ion concentration in the titrant solutions may be any suitable concentration, which is typically in the range from 0.01 to 1.0 M.

The first and second analysis cells may be the same cell or separate cells. Each analysis cell is preferably cleaned (or replaced) between analyses to minimize cross-contamination errors. Cleaning may be effected by any suitable method, water rinsing and drying, for example.

In some cases, purified water may be added to increase the volume of an analysis solution so that all appropriate components of the titration analysis system (electrodes and stirrer, for example) are adequately in contact with the analysis solution. Purified water may also be added to dilute a plating bath sample to facilitate solution handling. Purified water may be added using the same injector used for a cleaning system, or a different injector. Bath sample dilution changes the slopes of titration curves but typically does not affect the results of the analysis.

Analysis solutions should be stirred to facilitate mixing after each addition of a complexing agent or of an aliquot of a titrant solution to an analysis solution. Solution stirring may be provided by any suitable method, including magnetic stirring, electrical motor stirring, gas bubbling, ultrasonic agitation, or solution circulation, for example.

The $Cu^{2+}$ concentration parameter or parameters used to practice the invention may be any suitable parameter or parameters measured by any suitable method or methods. The back-titration and the titration of the invention may employ the same or different $Cu^{2+}$ concentration parameters measured by the same or different methods. Preferably, the same $Cu^{2+}$ concentration parameter measured by the same method is employed for both the back-titration and the titration of the invention.

One preferred $Cu^{2+}$ concentration parameter is the potential of a copper ion specific electrode measured relative to a reference electrode, which is proportional to the free copper ion concentration. The copper ion specific electrode and the reference electrode are placed in contact with the analysis solution and the potential of the copper ion specific electrode is measured using a voltmeter (having a sufficiently high input impedance). A combination electrode, comprising a copper ion specific electrode and a reference electrode in the same unit, may also be used. A simple beaker cell may be used with a copper ion specific electrode but a closed cell is preferably employed to facilitate automated cleaning and injection of standard solutions and titrant solutions.

In another preferred embodiment, the $Cu^{2+}$ concentration parameter is the light absorption or absorbance for a specific wavelength or wavelength range measured by a spectroscopic method using a spectrophotometer. The wavelength or wavelength range may be selected to reflect the concentration of free copper ions or weakly complexed copper ions, or both.

In still another preferred embodiment, the $Cu^{2+}$ concentration parameter is an electrochemical kinetic parameter measured by an electrochemical kinetic measurement. In this case, free $Cu^{2+}$ ions or weakly complexed copper ions are detected as a current or potential associated with electrochemical reaction of the copper ions under diffusion or hydrodynamic control. Commercial equipment for performing electrochemical analysis is readily available. As known to those skilled in the art, electrochemical measurements may be potentiometric or galvanostatic, and are generally performed using a working electrode (typically of an inert metal, such as platinum), a counter electrode (of any suitable material), a reference electrode (commercially available), a potentiostat (for controlling the working electrode potential or current), and a waveform generator to control the working electrode potential as a function of time (depending on the measurement method). A rotating disk electrode configuration may also be used to provide controlled hydrodynamic conditions at the working electrode surface.

Titration and back-titration endpoints according to the invention may be determined by standard procedures. Typically, a titration curve of the $Cu^{2+}$ concentration parameter as a function of the volume of titrant solution added to the analysis solution is generated. The titration or back-titration endpoint corresponds to a substantial increase in the $Cu^{2+}$ concentration parameter. The endpoint may be determined using any suitable titration curve feature, including an inflection point, a knee or a predetermined value for the $Cu^{2+}$ concentration parameter, for example. The titration or back-titration curve may also be differentiated, which converts an inflection point associated with the titration or back-titration endpoint to a peak providing a sharper endpoint. The titration and back-titration endpoints may also be determined by a computer using tabulated data.

The apparatus of the invention enables automated application of the method of the invention. The apparatus comprises: (A) at least one titration analysis system; (B) a computing device having a memory element with a stored algorithm operative to effect at least the basic steps, and preferably all of the steps, of the method of the invention; and (C) an interface enabling the computing device to control the titration analysis system or systems. Suitable titration analysis systems (and components thereof), computing devices, memory elements, and interfaces for use in the apparatus of the invention are well known to those skilled in the art.

FIG. 1 is a schematic representation of a preferred apparatus 100 of the invention, which comprises a computing device 101, a titration analysis system 102, and an interface 103 enabling computing device 101 to control titration analysis system 102 and acquire titration analysis data from titration analysis system 102. The arrows indicate the direction of flow of electrical control signals, acquired data, and the various solutions. Computing device 101 has a memory element 104 with a stored algorithm for effecting at least the basic steps of the method of the invention. Computing device 101 may comprise a computer with integrated components, or may comprise separate components, a microprocessor and a memory device that includes memory element 104, for example. Memory element 104 may be any one or a combination of available memory elements, including a computer hard drive, a microprocessor chip, a read-only memory (ROM) chip, a programmable read-only memory (PROM) chip, a magnetic storage device, a computer disk (CD) and a digital video disk (DVD), for example. Memory element 104 may be an integral part of computing device 101 or may be a separate device. Interface 103 may be an integral part of computing device 101 or may be a separate device. This preferred apparatus may be used to practice the various embodiments of the invention.

The preferred titration analysis system 102 depicted in FIG. 1 comprises: an analysis cell 111 containing an analysis solution 105; a sampling device 112 for adding a predetermined volume of a sample of the copper plating bath to analysis cell 111; a strong complexing agent injector 113 for making a standard addition of a strong complexing agent to the sample of the copper plating bath so as to provide a first analysis solution; a chemical injector 114 for making a standard addition of a hydroxide compound or the bath complexing agent, respectively, to the first analysis solution or a second analysis solution; a copper ion detector 115 for measuring a copper ion concentration parameter for analysis solution 105; a titrator device 119 for adding an aliquot of a known volume of a titrant solution to analysis solution 105; a solution stirring device 120 for stirring analysis solution 105; and a cell cleaning device 122 for cleaning analysis cell 111 to minimize cross-contamination between analyses. Two or more titration analysis systems may be used to reduce analysis time. In this case, the number of injector devices for one or more of the titration analysis systems may be reduced, depending on the analyses to be performed by the particular system.

The optimum design of analysis cell 111 depends on the method used to measure the $Cu^{2+}$ concentration parameter, among other factors. A simple beaker cell may be used with a copper ion specific electrode but a closed cell is preferred to facilitate automated cleaning and injection of standard solutions and titrant solutions. A cell used for spectroscopic measurement of the $Cu^{2+}$ concentration parameter preferably includes at least one optical window.

Sampling device 112, strong complexing agent injector 113, chemical injector 114 and titrator device 119 may comprise any suitable solution metering device, including a metering pump or syringe. A wide variety of such devices are available commercially.

In a preferred embodiment, copper ion detector 115 (FIG. 1) used to measure the $Cu^{2+}$ concentration parameter for analysis solution 105 comprises a copper ion specific electrode 116 in contact with analysis solution 105, a reference electrode 117 also in contact with analysis solution 105, and a voltmeter 118 for measuring the electrical potential difference between copper ion specific electrode 116 and reference electrode 117. Alternatively, the $Cu^{2+}$ concentration parameter may be determined by spectroscopic measurements or electrochemical kinetic measurements, or by any other suitable means. Suitable equipment for spectroscopic and electrochemical measurements is commercially available.

Solution stirring may be provided by a magnetic stirrer 120 coupled with a magnetic stir bar 121, as shown in FIG. 1, or by any other suitable solution stirring device, including an impellor driven by an electrical stirring motor, a gas bubbler, an ultrasonic wave generator, or a solution circulator, for example.

Cell cleaning device 122 (FIG. 1) preferably rinses the cell with purified water (pumped into the cell) and collects the rinse water for subsequent disposal. After being rinsed, the cell may also be blow dried to further reduce cross-contamination between the analyses of the invention.

A preferred computing device of the invention has a stored algorithm operative to effect the steps of the method, comprising: (1) making a standard addition of a predetermined quantity of a strong complexing agent to a first sample of the copper plating bath so as to provide a first analysis solution of known volume contained in a first analysis cell, said predetermined quantity of the strong complexing agent being substantially greater than that needed to fully complex all of the copper ions present in the first analysis solution; (2) providing a first titrant solution comprising a first predetermined concentration of copper ions; (3) performing a back-titration by repeatedly adding an aliquot of a known volume of the first titrant solution to the first analysis solution and measuring a first $Cu^{2+}$ concentration parameter for the first analysis solution; (4) determining a back-titration endpoint corresponding to a substantial increase in the first $Cu^{2+}$ concentration parameter measured for the first analysis solution; (5) calculating the concentration of copper ions in the copper plating bath based on the back-titration endpoint; (6) providing a second analysis solution contained in a second analysis cell; (7) providing a second titrant solution comprising a second predetermined concentration of copper ions; (8) performing a titration by repeatedly adding an aliquot of a known volume of the second titrant solution to the second analysis solution and measuring a second $Cu^{2+}$ concentration parameter for the second analysis solution; (9) determining a titration endpoint corresponding to a substantial increase in the second $Cu^{2+}$ concentration parameter measured for the second analysis solution; and (10) calculating a concentration of the bath complexing agent based on the titration endpoint. The stored algorithm is further operative to activate the solution stirring device so as to stir the analysis solution during the back-titration and the titration, and to activate the cell cleaning device so as to clean the analysis cell between the back-titration and the titration, and/or between analyses.

In a basic embodiment, the stored algorithm of the computing device of the invention is operative to effect only Steps (6)-(10) of the method of the invention so as to determine the concentration of free bath complexing agent in the copper plating bath. In this case, strong complexing agent injector 113 (FIG. 1) of the apparatus of the invention is not needed.

Description of a Preferred Embodiment

The efficacy of the invention for determining the concentrations of copper ions and complexing agent in an alkaline copper plating bath was demonstrated for a test bath having a pH of 10.4 and comprising 1.5 mM cupric sulfate, 4.0 mM EDA complexing agent, 1.25 mM boric acid, and 200 ppm tetramethylammonium hydroxide. Samples of the test bath were diluted with de-ionized water to provide an analysis solution volume of about 53 mL for which the copper ion concentration was less than 1.5 mM. Titrations and back-titrations were performed using a QLC-7000 analyzer with a titrator module (ECI Technology). The copper ion titrant solution was 25 mM cupric sulfate for all analyses. The $Cu^{2+}$ concentration parameter was the potential of a copper ion specific electrode (Model 9429 BN (Thermo Orion) measured relative to a silver-silver chloride (SSCE) reference electrode (4 M KCl solution) using the high-impedance voltmeter of the QLC-7000 analyzer. The strong complexing agent used for the copper ion analysis was disodium ethylenediaminetetraacetic acid ($Na_2H_2EDTA$) added as a 0.1 M solution. The endpoint for both the titration and back-titration was taken as the peak (maximum slope) in the differentiated titration curve, which corresponded to an inflection point in the titration curve.

Figure 2:
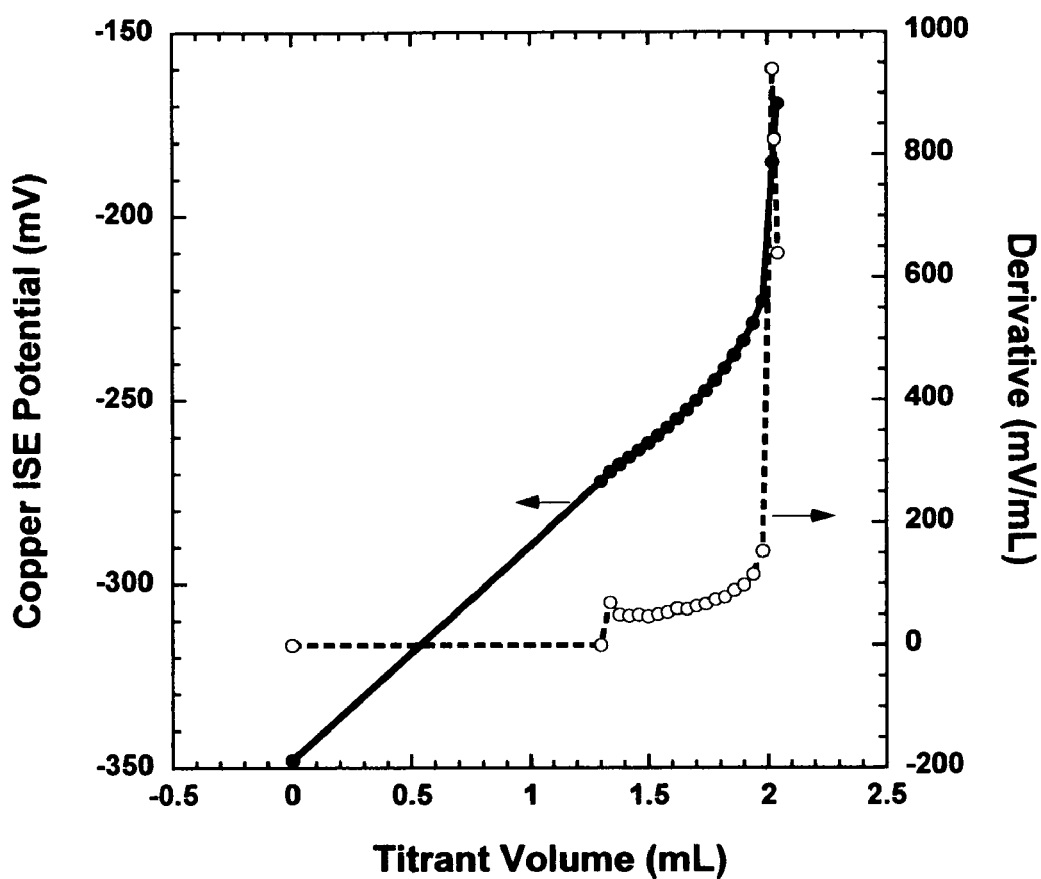
FIG. 2 shows a back-titration curve and differentiated back-titration curve of the potential of a copper ion specific electrode as a function of the volume of copper ion titrant solution (25 mM $CuSO_4$) added to a first analysis solution formed by adding 0.1 M $Na_2H_2EDTA$ solution to a first diluted sample of an alkaline copper plating bath (pH of 10.4) containing 1.5 mM cupric sulfate, 4.0 mM EDA complexing agent, 1.25 mM boric acid, and 200 ppm tetramethylammonium hydroxide. The back-titration endpoint provides a measure of the copper ion concentration in the plating bath.

FIG. 2 shows a back-titration curve and a differentiated back-titration curve of the potential of a copper ion specific electrode as a function of the volume of copper ion titrant (25 mM cupric sulfate) added to a first analysis solution comprising 1.5 mM $Na_2H_2EDTA$ added by standard addition of a 0.1 M $Na_2H_2EDTA$ solution to a first diluted sample of the test bath. The back-titration endpoint is evident as an inflection in the back-titration curve and a peak in the differentiated back-titration curve corresponding to a substantial increase in the free copper ion concentration in the analysis solution. The back-titration endpoint provides a measure of the copper ion concentration initially present in the plating bath sample. The molar ratio of EDTA to Cu ion at the titration endpoint is one. The total concentration of copper ions (free and complexed) in the plating bath sample can be calculated using the equation:

moles $Cu^{2+}$ in bath sample=moles EDTA added−
moles $Cu^{2+}$ titrated and taking into account the solution volumes involved. The molar concentration of copper ions in the copper plating bath is the number of moles of copper ions in the bath sample divided by the volume of the bath sample.

Figure 3:
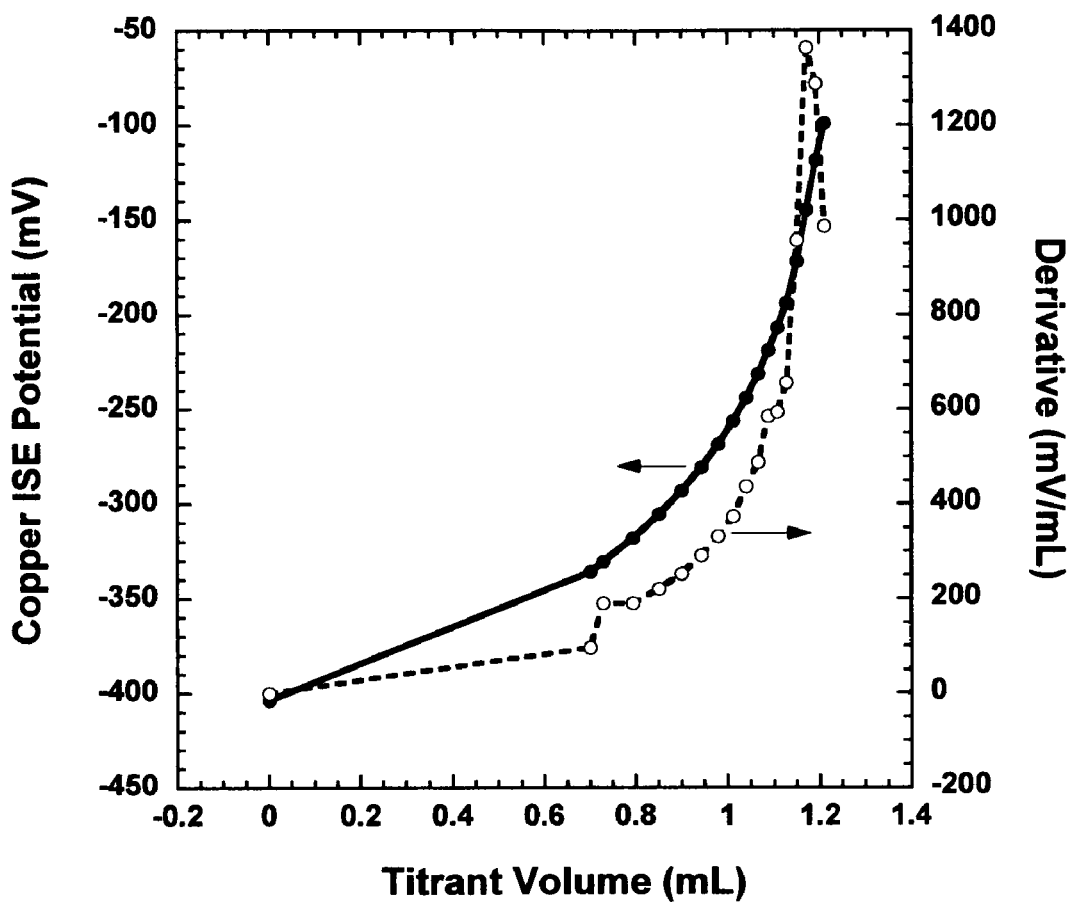
FIG. 3 shows a titration curve and differentiated titration curve of the potential of a copper ion specific electrode as a function of the volume of copper ion titrant solution (25 mM $CuSO_4$) added to a second analysis solution formed by standard addition of 50 mM EDA solution to a second diluted sample of the copper plating bath of FIG. 2. The titration endpoint provides a measure of the free EDA concentration in the plating bath.

FIG. 3 shows a titration curve and a differentiated titration curve of the potential of a copper ion specific electrode as a function of the volume of the copper ion titrant solution (25 mM cupric sulfate) added to a second analysis solution comprising an additional 0.75 mM EDA added by standard addition of a 50 mM EDA solution to a second diluted sample of the test bath. The titration endpoint is evident as an inflection point in the titration curve and a peak in the differentiated titration curve corresponding to a substantial increase in the free copper ion concentration in the analysis solution. The titration endpoint provides a measure of the free EDA concentration in the plating bath. The molar ratio of EDA to Cu ion at the titration endpoint is two. The total concentration of EDA complexing agent (free and copper complexed) in the plating bath sample is given by the equation:

moles free EDA in sample=2(moles $Cu^{2+}$ titrated)−
moles EDA added.

The molar concentration of free EDA in the copper plating bath is the number of moles of free EDA in the bath sample divided by the volume of the bath sample.

Table 1 summarizes the results for a series of 10 measurements of the copper ion concentration and free EDA concentration for the test bath, for which two analysis solutions were employed. Calculated results for the total EDA concentration are also included. Good accuracy and precision for the method and apparatus of the invention are evident.

TABLE 1

Bath Analysis Results For Separate Analysis Solutions

|  | Copper Ion | Free EDA | Total EDA |
| --- | --- | --- | --- |
| Expected (mM) | 1.5 | 1.0 | 4.0 |
| Average (mM) | 1.5 | 0.98 | 3.98 |
| Accuracy (%) | 0 | 2.4 | 0.6 |
| Std. Deviation | 0.02 | 0.05 | 0.05 |
| RSD (%) | 1.7 | 1.9 | 1.1 |

Figure 4:
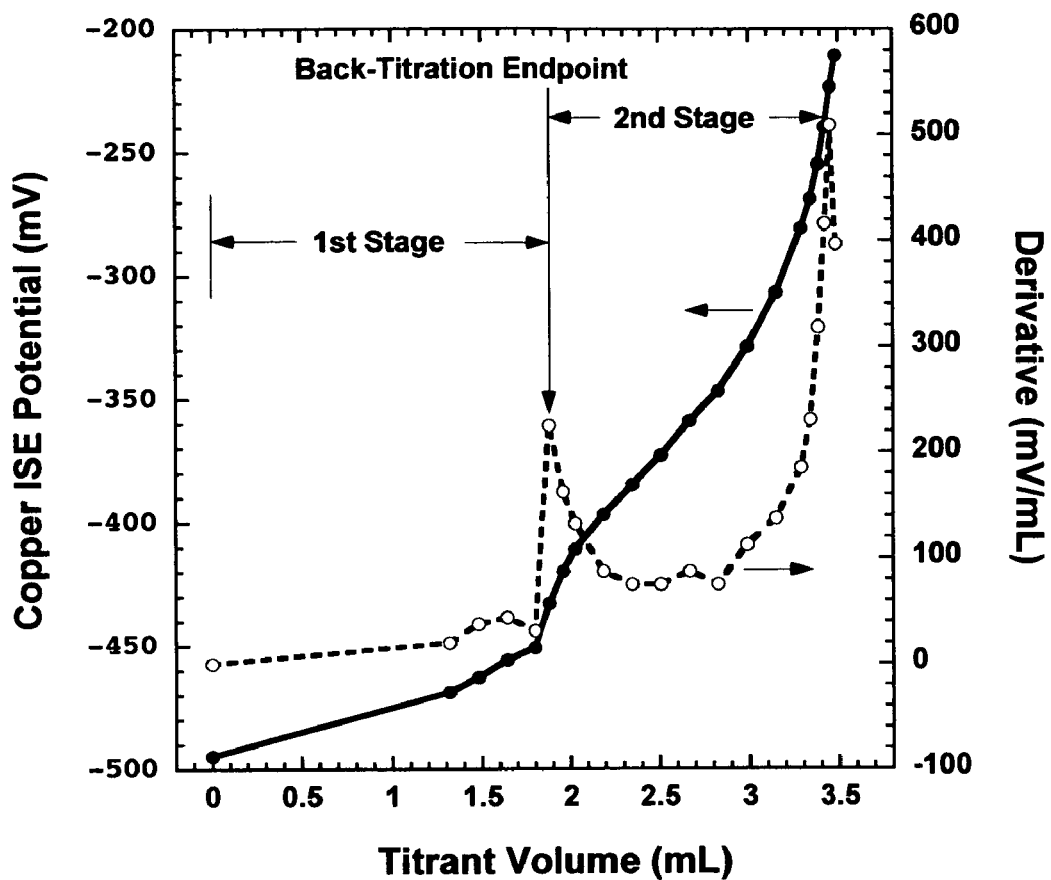
FIG. 4 shows a two-stage titration curve and differentiated two-stage titration curve of the potential of a copper ion specific electrode as a function of the volume of copper ion titrant solution (25 mM $CuSO_4$) added to a third analysis solution formed by standard addition of a 0.1 M $Na_2H_2EDTA$ solution and a 1.0 M NaOH solution to a third diluted sample of the copper plating bath of FIG. 2. The back-titration endpoint (first stage) provides a measure of the copper ion concentration in the plating bath, and the titration endpoint (second stage) provides a measure of the total concentration of bath complexing agent.

FIG. 4 shows a two-stage titration curve and a differentiated two-stage titration curve of the potential of a copper ion specific electrode as a function of the volume of copper ion titrant solution (25 mM cupric sulfate) added to a third analysis solution comprising 1.5 mM $Na_2H_2EDTA$ added by standard addition of a 0.1 M $Na_2H_2EDTA$ solution and 3.0 mM NaOH added by standard addition of a 1.0 M NaOH solution to a third diluted sample of the test bath. Endpoints for the back-titration and titration stages are evident as inflections in the two-stage titration curve and peaks in the differentiated two-stage titration curve corresponding to a substantial increase in the free copper ion concentration in the analysis solution. The copper ion concentration was calculated from the volume of titrant solution added to the analysis solution up to the first endpoint (back-titration stage), and the total bath complexing agent concentration was calculated from the volume of additional titrant solution added from the first endpoint to the second endpoint (titration stage).

Figure 5:
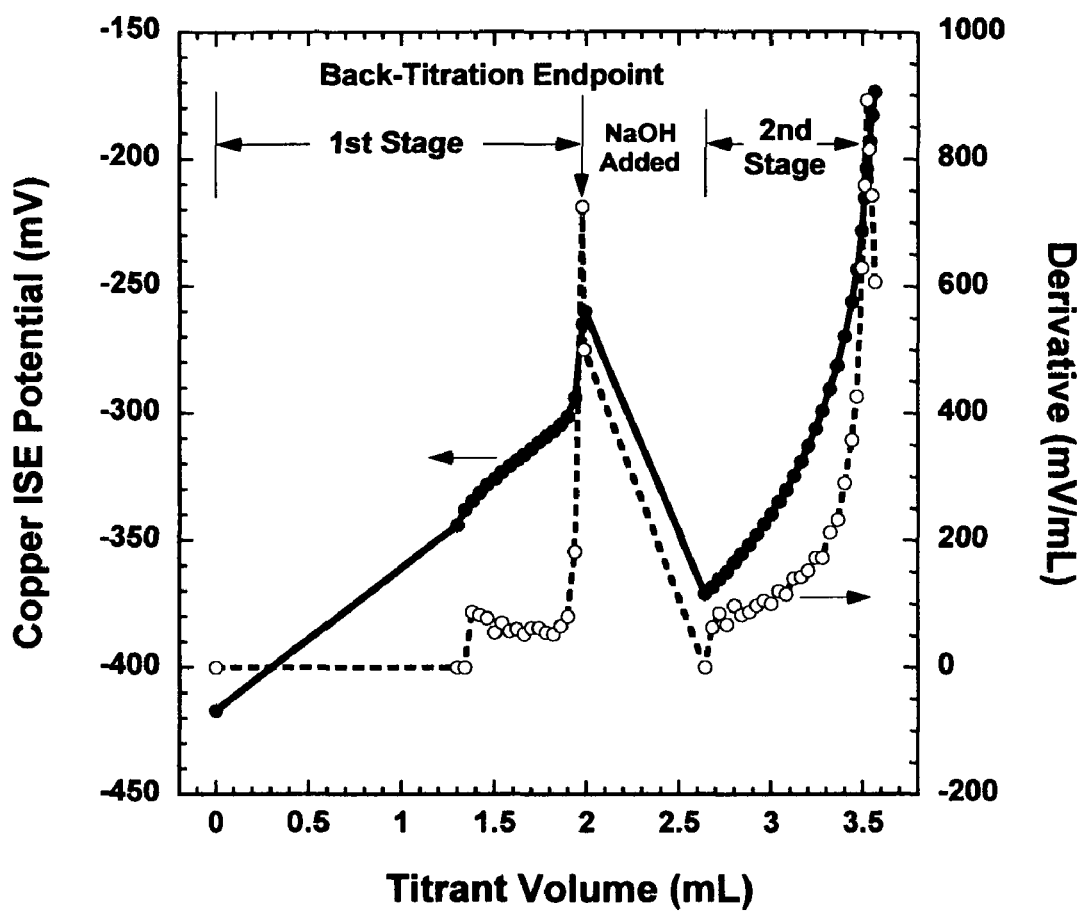
FIG. 5 shows a two-stage titration curve and differentiated two-stage titration curve of the potential of a copper ion specific electrode as a function of the volume of copper ion titrant solution (25 mM $CuSO_4$) added to a fourth analysis solution formed by standard addition of a 0.1 M $Na_2H_2EDTA$ solution to a fourth diluted sample of the copper plating bath of FIG. 2, to which 1.0 M NaOH solution was added after the back-titration endpoint (rather than at the beginning of the analysis as for FIG. 4).

FIG. 5 shows a two-stage titration curve and a differentiated two-stage titration curve of the potential of a copper ion specific electrode as a function of the volume of copper ion titrant solution (25 mM cupric sulfate) added to a fourth analysis solution comprising 1.5 mM $Na_2H_2EDTA$ added before the back-titration by standard addition of a 0.1 M $Na_2H_2EDTA$ solution to a fourth diluted sample of the test bath, and further comprising 3.0 mM NaOH added after the back-titration by standard addition of a 1.0 M NaOH solution to the fourth analysis solution. Endpoints for the back-titration and titration stages are evident as inflections in the two-stage titration curve and peaks in the differentiated two-stage titration curve corresponding to a substantial increases in the free copper ion concentration in the analysis solution. The copper ion concentration was calculated from the volume of titrant solution added to the analysis solution up to the first endpoint (back-titration stage), and the total bath complexing agent concentration was calculated from the volume of additional titrant solution added from the first endpoint to the second endpoint (titration stage).

Table 2 summarizes the results for a series of 5 measurements of the copper ion concentration and total EDA concentration for the test bath via a two-stage titration involving addition of $Na_2H_2EDTA$ to the analysis solution before the back-titration and addition of NaOH after the back-titration. Calculated results for the free EDA concentration are also included. Good accuracy and precision for the method and apparatus of the invention are evident.

TABLE 2

| Bath Analysis Results for Two-Stage Titration | | | |
|---|---|---|---|
| | Copper Ion | Free EDA | Total EDA |
| Expected (mM) | 1.5 | 1.0 | 4.0 |
| Average (mM) | 1.46 | 1.0 | 3.96 |
| Accuracy (%) | 2.5 | 2.0 | 1.1 |
| Std. Deviation | 0.03 | 0.05 | 0.03 |
| RSD (%) | 2.0 | 4.8 | 0.7 |

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for analyzing a copper plating bath comprising copper ions and a bath complexing agent, comprising the steps of:
   (1) making a standard addition of a predetermined quantity of a strong complexing agent to a first sample of the copper plating bath so as to provide a first analysis solution of known volume contained in a first analysis cell, said predetermined quantity of the strong complexing agent being substantially greater than that needed to fully complex all of the copper ions present in the first analysis solution;
   (2) providing a first titrant solution comprising a first predetermined concentration of copper ions;
   (3) performing a back-titration by repeatedly adding an aliquot of a known volume of the first titrant solution to the first analysis solution and measuring a first $Cu^{2+}$ concentration parameter for the first analysis solution;
   (4) determining a back-titration endpoint corresponding to a substantial increase in the first $Cu^{2+}$ concentration parameter measured for the first analysis solution;
   (5) calculating the concentration of copper ions in the copper plating bath based on the back-titration endpoint;
   (6) providing a second analysis solution contained in a second analysis cell;
   (7) providing a second titrant solution comprising a second predetermined concentration of copper ions;
   (8) performing a titration by repeatedly adding an aliquot of a known volume of the second titrant solution to the second analysis solution and measuring a second $Cu^{2+}$ concentration parameter for the second analysis solution;
   (9) determining a titration endpoint corresponding to a substantial increase in the second $Cu^{2+}$ concentration parameter measured for the second analysis solution; and
   (10) calculating a concentration of the bath complexing agent based on the titration endpoint.

2. The method of claim 1, wherein the first and second titrant solutions are the same titrant solution, are different titrant solutions having the same chemical composition, or are different titrant solutions having the same chemical constituents at different concentrations.

3. The method of claim 1, wherein the first and second analysis cells are the same analysis cell.

4. The method of claim 1, wherein the first and second $Cu^{2+}$ concentration parameters are measured by a method selected from the group consisting of copper ion specific electrode measurements, spectroscopic measurements, electrochemical kinetic measurements, and combinations thereof.

5. The method of claim 1, wherein the first and second $Cu^{2+}$ concentration parameters are the same parameter.

6. The method of claim 1, wherein the second analysis solution provided in Step (6) is the first analysis solution from Step (3) such that the same bath sample and the same analysis cell are used for both the back-titration of Step (3) and the titration of Step (8), and the concentration calculated in Step (10) is the total concentration of the bath complexing agent in the copper plating bath.

7. The method of claim 1, wherein the second analysis solution provided in Step (6) comprises a predetermined quantity of a hydroxide compound added by standard addition to the first analysis solution from Step (3) such that the same bath sample and the same analysis cell are used for both the back-titration of Step (3) and the titration of Step (8), and the concentration calculated in Step (10) is the total concentration of the bath complexing agent in the copper plating bath.

8. The method of claim 7, wherein the hydroxide compound is selected from the group consisting of sodium hydroxide, potassium hydroxide, ammonium hydroxide, a tetraalkylammonium hydroxide, and combinations thereof.

9. The method of claim 1, wherein the second analysis solution provided in Step (6) comprises a predetermined quantity of the bath complexing agent added by standard addition to a second sample of the plating bath, said predetermined quantity of the bath complexing agent being substantially greater than that needed to result in full complexation of the copper ions present in the second analysis solution, and the concentration calculated in Step (10) is the concentration of free bath complexing agent in the copper plating bath.

10. The method of claim 1, wherein the copper plating bath has a pH in the range from 9 to 13, and comprises copper ions having a concentration in the range from 0.001 to 1.0 M, a complexing agent having a molar ratio in the range from 1 to 4 relative to the concentration of copper ions, and optionally boric acid having a concentration in the range from 0.001 to 0.5 M.

11. The method of claim 1, wherein the bath complexing agent is selected from the group consisting of ethylene diamine (EDA), citric acid, and salts thereof.

12. The method of claim 1, wherein the source of copper ions in at least one of the copper plating bath, the first titrant solution and the second titrant solution is cupric sulfate.

13. The method of claim 1, wherein the strong complexing agent is EDTA, and the bath complexing agent is ethylene diamine (EDA) or citric acid.

14. A method for determining the concentrations of copper ions and ethylene diamine (EDA) complexing agent in a copper plating bath, comprising the steps of:
   (1) making a standard addition of a predetermined quantity of an EDTA complexing agent to a first sample of the copper plating bath so as to provide an analysis solution of known volume contained in an analysis cell, said predetermined quantity of the EDTA complexing agent being substantially greater than that needed to fully complex all of the copper ions present in the analysis solution;

(2) providing a titrant solution comprising a predetermined concentration of copper ions;

(3) performing a back-titration by repeatedly adding an aliquot of a known volume of the titrant solution to the analysis solution and measuring a $Cu^{2+}$ concentration parameter for the analysis solution using a copper ion specific electrode;

(4) determining a back-titration endpoint corresponding to a substantial increase in the $Cu^{2+}$ concentration parameter measured for the analysis solution;

(5) calculating the copper ion concentration in the copper plating bath based on the back-titration endpoint;

(6) performing a titration by repeatedly adding an aliquot of a known volume of the titrant solution to the analysis solution from Step (3) and measuring the $Cu^{2+}$ concentration parameter for the analysis solution;

(7) determining a titration endpoint corresponding to a substantial increase in the $Cu^{2+}$ concentration parameter measured for the analysis solution; and (7) calculating the total EDA concentration in the copper plating bath based on the titration endpoint, and optionally the free EDA concentration, wherein the copper plating bath has a pH in the range from 9 to 13, the concentration of copper ions in the copper plating bath is in the range from 0.001 to 1.0 M, the concentration of the EDA complexing agent is in the range from 0.001 to 4.0 M, and the bath optionally contains boric acid having a concentration in the range from 0.001 to 0.5 M.

15. The method of claim 14, wherein a predetermined quantity of a hydroxide compound is added by standard addition to the analysis solution before Step (6).

* * * * *